(12) United States Patent
Andersen

(10) Patent No.: US 8,986,668 B2
(45) Date of Patent: Mar. 24, 2015

(54) METHOD OF MANUFACTURING A NICOTINE DELIVERY PRODUCT

(75) Inventor: Carsten Andersen, Vejle (DK)

(73) Assignee: Fertin Pharma A/S, Vejle (DK)

( * ) Notice: Subject to any disclaimer, the term of this patent is extended or adjusted under 35 U.S.C. 154(b) by 1199 days.

(21) Appl. No.: 11/921,199

(22) PCT Filed: Jun. 1, 2006

(86) PCT No.: PCT/DK2006/000307
§ 371 (c)(1),
(2), (4) Date: Nov. 21, 2008

(87) PCT Pub. No.: WO2006/028468
PCT Pub. Date: Dec. 7, 2006

(65) Prior Publication Data
US 2009/0092573 A1  Apr. 9, 2009

(30) Foreign Application Priority Data
Jun. 1, 2005  (DK) .................... 2005 00796

(51) Int. Cl.
*A61K 9/68* (2006.01)
*A61K 31/465* (2006.01)
*A61K 47/48* (2006.01)

(52) U.S. Cl.
CPC ......... *A61K 47/48184* (2013.01); *A61K 9/0058* (2013.01); *A61K 31/465* (2013.01)
USPC ...................................... 424/78.1

(58) Field of Classification Search
USPC ............................................ 424/78.1
See application file for complete search history.

(56) References Cited

U.S. PATENT DOCUMENTS

| | | | |
|---|---|---|---|
| 3,845,217 A * | 10/1974 | Ferno et al. ............ 426/3 |
| 3,901,248 A | 8/1975 | Lichtneckert et al. |
| 6,586,449 B1 | 7/2003 | Walling |
| 2002/0015687 A1 | 2/2002 | Bellamy et al. |

FOREIGN PATENT DOCUMENTS

| WO | 03/061709 A1 | 7/2003 |
| WO | 2005/053691 A2 | 6/2005 |

OTHER PUBLICATIONS

Form PCT/ISA/210, WO, Dec. 9, 2006, ISR for PCT/DK2006/000307.

* cited by examiner

*Primary Examiner* — Michael G Hartley
*Assistant Examiner* — Robert Cabral
(74) *Attorney, Agent, or Firm* — Merchant & Gould P.C.

(57) ABSTRACT

A method of manufacturing a nicotine delivery product comprising nicotine and a cation exchange resin. More precisely, to a method for preparing a nicotine delivery product said method comprising (a) mixing nicotine, a cation exchange resin, an organic polyol and water to form a mixture wherein the total amount of water is from 26 to 45% by weight of the total mixture, and (b) removing water from the mixture to produce said nicotine delivery product.

14 Claims, No Drawings

METHOD OF MANUFACTURING A NICOTINE DELIVERY PRODUCT

This application is the U.S. national phase application, pursuant to 35 U.S.C. §371, of PCT international application Ser. No. PCT/DK2006/000307, filed Jun. 1, 2006, designating the United States and published in English on Dec. 7, 2006 as publication WO 2006/128468 A1, which claims priority to Denmark application Ser. No. PA 2005 00796, filed Jun. 1, 2005. The entire contents of the aforementioned patent applications are incorporated herein by this reference.

FIELD OF THE INVENTION

The present invention relates to methods for manufacturing nicotine delivery products.

BACKGROUND OF THE INVENTION

Nicotine is a well known, highly characterized alkaloid that can be isolated from the dried leaves of *Nicotiana tabacum*. Its numerous commercial uses include utilities such as a fumigant, an insecticide and the like. It is of therapeutically valuable in the treatment of the smoking withdrawal syndrome. This treatment is based on the fact that the administration of nicotine into the body has been readily accomplished by the method of smoking, e.g., from cigarettes, pipes or cigars. The smoker experiences a satisfactory sensation from such administration. However, smoking may be associated with health hazards not necessarily associated with administration of nicotine itself.

As a result, non-smoking methods have been devised to administer nicotine to the body. These include nicotine containing chewing gums, nicotine-impregnated dermal patches, nicotine inhalers and the like. A variety of patents have disclosed such products.

U.S. Pat. No. 4,692,462 discloses a transdermal drug delivery system having a drug reservoir composed, in part, of an ion exchange resin. The drug reservoir also contains water and a hydrophilic polymer gel. The presence of the water causes the drug to become unbound and therefore to have a disadvantageously short shelf life.

U.S. Pat. No. 3,901,248 discloses a chewable smoking substitute composition which comprises a chewing gum base and a nicotine/cation exchange resin complex dispersed in said gum base. When such composition is chewed, nicotine is released in small and reduced amounts into the mouth, within the first few minutes of chewing. The composition is marginally effective in inducing the pleasurable sensation of smoking that is typically desired from those engaged in the therapy that incorporates such chewing gum. There is no disclosure of a polyol in intimate contact with a nicotine/cation exchange resin complex, only a disclosure of the use of a minor amount of glycerol as a softener for the chewing gum base.

U.S. Pat. No. 6,586,449 claims a method for preparing a nicotine composition having a nicotine release rate of not less than 70% over a 10 minute period said method comprising (a) mixing an aqueous solution of an organic polyol with a cation exchange resin selected from the group consisting of (i)—a methacrylic, weakly acidic type of resin containing carboxylic functional groups, (ii)—a polystyrene, strongly acidic type of resin containing sulphonic functional groups, and (iii)—a polystyrene, intermediate acidic type of resin containing phosphonic functional groups, thereby forming a cation exchange resin mixture having some of its ion exchange sites partially blocked with said polyol; (b) admixing with said mixture of step (a) an aqueous solution of nicotine to form a nicotine-coated cation exchange resin admixture; and (c) removing water from said admixture to produce said nicotine composition having a nicotine release rate of not less than 70% over a 10 minute period.

This patent teaches that in carrying out the claimed process it is necessary to combine the organic polyol with the cation exchange resin to form a mixture (slurry) before adding nicotine. Thereby a cation exchange resin mixture is formed having some of its ion exchange sites partially blocked with said polyol. To the mixture thus formed is admixed an aqueous solution of nicotine, and the admixture is then dried to remove the water. According to the Examples, release rates of nicotine from dried compositions prepared in this way with different polyols were in the range of 70-77%, as compared to 65-66% without polyol, over a 10 minute period when determined according to the procedure set forth in the U.S.P. Official Monograph, Volume 25, pages 1225 and 1226.

When mixing a cation exchange resin, a polyol, and nicotine, U.S. Pat. No. 6,586,449 teaches preparation of an aqueous slurry as an intermediate which requires the removal of a considerable amount of water for isolating the nicotine delivery product comprising nicotine, a cation exchange resin and a polyol which is time consuming and requires a considerable amount of energy for evaporating the water. Furthermore, the amounts of water needed reduces the capacity of a given production plant.

It has now surprisingly been found that when mixing a cation exchange resin, a polyol, and nicotine it is not necessary to produce a slurry in order to obtain a satisfactory mixing of the constituents for obtaining a product being sufficiently homogeneous and showing the desired release properties. Thus, it has been found that it is only necessary to add a relatively small amount of water together with the other constituents, namely an amount sufficient to produce a soft and plastic mixture (a paste), in order to produce a product comprising a cation exchange resin, a polyol, and nicotine being sufficient homogeneous and showing the required release properties.

SUMMARY OF THE INVENTION

The present invention relates to a method for preparing a nicotine delivery product said method comprising (a) mixing nicotine, a cation exchange resin and water to form a mixture wherein the total amount of water is from 30 to 60% by weight of the total mixture, and (b) removing water from the mixture to produce said nicotine delivery product.

In a second aspect the present invention relates to a method for preparing a nicotine delivery product said method comprising (a) mixing nicotine, a cation exchange resin, an organic polyol and water to form a mixture wherein the total amount of water is from 26 to 45% by weight of the total mixture, and (b) removing water from the mixture to produce said nicotine delivery product.

In a third aspect the present invention relates to a method for preparing a nicotine delivery product said method comprising (a) mixing an aqueous suspension of a nicotine/cation exchange resin complex with an organic polyol or an aqueous solution or suspension thereof forming a mixture wherein the total amount of water is from 26 to 45% by weight of the total mixture, and (b) removing water from the mixture to produce said nicotine delivery product.

In a fourth aspect the invention relates to a method for preparing a nicotine delivery product said method comprising
(a) mixing an aqueous solution of nicotine with a cation exchange resin forming a nicotine/cation exchange resin complex, (b) admixing to said complex of step (a) an aqueous solution or suspension of an organic polyol to form an aqueous mixture of nicotine/cation exchange resin complex incorporating the polyol wherein the total amount of water is from 26 to 45% by weight of the total mixture, and (c) removing water from said mixture to produce said nicotine delivery product.

In a fifth aspect the invention relates to a nicotine delivery product obtained by a method according to the invention.

In a sixth aspect the invention relates to a chewable gum composition comprising a chewing gum base and a nicotine delivery product prepared by the method of the invention substantially uniformly distributed in said chewing gum base.

DETAILED DESCRIPTION

The present invention relates to a method for preparing a nicotine delivery product said method comprising (a) mixing nicotine, a cation exchange resin and water to form a mixture wherein the total amount of water is from 30 to 60% by weight of the total mixture, and (b) removing water from the mixture to produce said nicotine delivery product.

The present invention also relates to a method for preparing a nicotine delivery product said method comprising (a) mixing nicotine, a cation exchange resin, an organic polyol and water to form a mixture wherein the total amount of water is from 26 to 45% by weight of the total mixture, and (b) removing water from the mixture to produce said nicotine delivery product.

The present invention also relates to a method for preparing a nicotine delivery product said method comprising (a) mixing an aqueous suspension of a nicotine/cation exchange resin complex with an organic polyol or an aqueous solution or suspension thereof forming a mixture wherein the total amount of water is from 26 to 45% by weight of the total mixture, and (b) removing water from the mixture to produce said nicotine delivery product.

It has surprisingly been found that when mixing a nicotine/cation exchange resin complex of the kind described in U.S. Pat. No. 3,901,248 with an organic polyol in aqueous solution in the presence of an amount of water in the mixture of from 26 to 45% by weight and drying the resulting product, a nicotine delivery product is obtained which has the same nicotine loading capacity as the compositions disclosed in U.S. Pat. No. 3,901,248 and U.S. Pat. No. 6,586,449, and showing at least as high a release rate of nicotine, i.e. at least 70% over a 10 minute period when determined as described in more detail in the U.S.P. Official Monograph, Volume 26, pages 1309-1310.

Any non-ionic pharmaceutical grade cationic ion exchange resin used to bind anionic molecules at the ion exchange sites may be employed in the present invention. Examples of such cationic materials are: those bearing a carboxylic acid group, such as a weakly acidic type of resins containing carboxylic functional groups (these resins are typically derived from polymers or copolymers of methacrylic acid or polymethacrylic acid); the strongly acidic type of resins containing sulphonic functional groups (these resins are typically derived from polymers of styrene or copolymers of styrene and divinylbenzene); or the intermediate acidic type of resins containing phosphonic acid functional groups (these resins are typically derived from polymers of styrene or copolymers of styrene and divinylbenzene).

Cationic ion exchange resins are well known in the art and the present invention encompasses all of these. A preferred cation exchange resin is a methacrylic, weakly acidic type of resin containing carboxylic functional groups. Representative cation exchange resins suitable for use in accordance with the present invention are disclosed in U.S. Pat. No. 3,901,248. The preferred cation exchange resins are those known in the art as the Amberlite® resins from Rohm and Haas, Paris, Cedex, France and include, for example, Amberlite® IR20, Amberlite® IRP69, Amberlite® IRP64, Amberlite® IRP58, Amberlite® IRC50, and Amberlite® IRP69. Preferred cation exchange resins are polacrilex ion exchange resin (Amberlite® IRP64) and a weak acidic exchange resin Purolite C115HMR from Purolite.

Suitable organic polyols for use according to the present invention are non-toxic C2 to C12 linear or branched hydrocarbons having at least 2 hydroxyl groups preferably selected from the group consisting of 1,2-propanediol, 1,3-propanediol, 1,6-hexanediol, glycerol and sorbitol and non-toxic C5 to C12 cyclic or heterocyclic hydrocarbons having at least 2 hydroxyl groups, preferably selected from the group consisting of hexahydroxyl cyclohexane (inositol) and mono- and disaccharides.

Preferred cyclic or heterocyclic organic polyols are glucose, fructose and sucrose.

The presence of a polyol also facilitates improved handling of the nicotine delivery product because it reduces the release of dust from the material.

In a preferred embodiment of the invention, the total amount of water present in the mixture is from 30 to 40% by weight of the total mixture, more preferred about 35% by weight of the total mixture. In an embodiment of the invention the total amount of water present in the mixture is from 26 to 35% by weight of the total mixture. In another embodiment of the invention the total amount of water present in the mixture is from 35 to 46% by weight of the total mixture.

Without limiting the invention to any specific hypothesis it is believed that the high release rate observed for products according to the present invention may be explained below.

In a product without polyol, the binding between nicotine and the cationic resin is dominated by ionic bonds.

The same type of binding is found in the product according to the present invention, but is believed to be covered by the added polyol giving a high concentration of polyol on the surface of the particles.

In the process disclosed in U.S. Pat. No. 6,586,449 a fraction of the ionic binding sites are physically blocked by the polyol which will also penetrate deeper into the resin particles before it is loaded with nicotine. The particles will therefore have a relatively high concentration of polyol in the centre and nicotine located on the surface.

In the release test according to the U.S.P. monograph the product is treated with a solution containing sodium chloride ions, which will cause an ion exchange reaction with the nicotine resin complex resulting in the release of the ionically bound nicotine.

It is believed that the polyol will act as a humectant during the release test and thus give rise to a better contact between the resin complex and the test solution. This effect will be more pronounced for the product of the present invention due to the very high concentration of polyol on the surface of the resin complex particles, which may explain the observed difference in release rates.

In a second aspect the invention relates to a method for preparing a nicotine delivery product said method comprising (a) mixing an aqueous solution of nicotine with a cation exchange resin forming a nicotine/cation exchange resin complex, (b) admixing to said complex of step (a) an aqueous solution or suspension of an organic polyol to form an aqueous mixture of nicotine/cation exchange resin complex incorporating the polyol wherein the total amount of water is from 26 to 45% by weight of the total mixture, and (c) removing water from said mixture to produce said nicotine delivery product.

Preferred cation exchange resins for use according to the present invention may be selected from the group consisting of
  (i) a methacrylic, weakly acidic type of resin containing carboxylic functional groups
  (ii) a polystyrene, strongly acidic type of resin containing sulphonic functional groups, and
  (iii) a polystyrene, intermediate acidic type of resin containing phosphonic functional groups.

It has been found suitable to use solutions of nicotine in the form of aqueous solutions comprising nicotine in an amount from about 5% by weight to about 50% by weight.

In the process according to the present invention the ratio of cation exchange resin to nicotine is suitably from about 1:1 to about 10:1, preferably from 2:1 to 6:1, and most preferred about 4:1.

In the process according to this invention the ratio of resin to polyol is suitably from about 1:1 to about 10:1, preferably from 2:1 to 8:1, and most preferred about 2,4:1.

In a preferred embodiment, the invention relates to a method for preparing a nicotine delivery product having a nicotine release rate of at least 80% over a 10 minute period, said method comprising
  (a) mixing an aqueous solution of nicotine with a cation exchange resin selected from the group consisting of
    (i) a methacrylic, weakly acidic type of resin containing carboxylic functional groups,
    (ii) a polystyrene, strongly acidic type of resin containing sulphonic functional groups, and
    (iii) a polystyrene, intermediate acidic type of resin containing phosphonic functional groups
  thereby forming a nicotine/cation exchange resin complex,
  (b) admixing with said complex of step (a) an organic polyol or an aqueous solution thereof to form an aqueous mixture of nicotine/cation exchange resin complex incorporating polyol, and
  (c) removing water from said mixture to produce said nicotine delivery product.

The nicotine delivery products obtained by a method according to the invention are also considered an aspect of the invention.

In a fourth aspect the invention relates to a chewable gum composition comprising a chewing gum base and a nicotine delivery product prepared by the method defined in any of claims 1-21 substantially uniformly distributed in said chewing gum base.

In another preferred embodiment of the invention the nicotine delivery product is an intermediate product for use in the manufacture of a nicotine delivery product such as a chewing gum. A number of such chewing gums are described in e.g. WO 2006/000232 A1 which is hereby incorporated by reference. The chewing gum may comprise additional polyols.

Examples of such polyols are:

C3
  1,2 Propanediol (propylene glycol), 1,3 propanediol (trimethylene glycol), or 1,2,3 propanetriol (glycerol);
C4
  Erythritol;
C5
  Xylitol;
C6
  Sorbitol, mannitol, 1,6 hexanediol, or cyclohexanehexol (inositol);
C12
  Maltitol, maltitol syrup, lactitol, or isomalt;
Mono- and Disaccharides
  Glucose, glucose syrup, fructose, or sucrose.

The resulting aqueous mixture of the nicotine/cation exchange resin complex with adsorbed organic polyol is then dried to remove the water. Such drying can be carried out by any conventional means, i.e. dried over a purge of nitrogen, dried under vacuum, etc. However, during the drying procedure temperatures in excess of 75-80° C. should be avoided as this may cause loss of nicotine. Preferably, the temperature should be kept below 60° C.

The dried product is typically milled and/or sieved to a substantially uniform particle size before being used.

The nicotine delivery product according to this invention is particularly suited for use in smoking substitution devices delivering nicotine such as chewing gum, patches, lozenges, melting tablets and tablets for chewing.

EXAMPLES

The following Examples illustrate the method of the present invention and the nicotine delivery product resulting from such method. These Examples should not be regarded as limiting the invention in any sense.

Materials And Methods

Nicotine, in accordance with USP
Water: Purified in accordance with USP
Glycerol, in accordance with USP
Equipment
  The following equipment was used in the below Examples:
  A sealable Diosna Multi Mixer VAC 150 having a cylindrical mixing vessel of 150 liters equipped with scraper and stirrer and a "chopper" for comminuting agglomerates and lumps. Furthermore, the lid is provided with a temperature sensor stretching into the product mass and a vacuum outlet having a filter. Introduction of air is effected in the bottom of the mixer.
  At the bottom of the mixer is an outlet for withdrawal of product.
  A Quadro mill Procedure for Producing a Nicotine Delivery Product The mixer was charged with water 1, and nicotine was weighed and added, and the nicotine container was rinsed with water 2 which was also added to the mixer. The mixer was closed and stirred for 5 minutes. Then ion exchange resin Amberlite® IRP64 was weighed and added to the mixer. The mixer was closed and stirred for 10 minutes.

Then, glycerol was weighed and added to the mixer, and the nicotine container was rinsed with water 3 which was also added to the mixer. The mixer was closed and stirred for 15 minutes.

The vacuum was connected and the mixture was dried by heating to maximum 60° C. under vacuum at a pressure of about 30-100 mbar (about 25-75 mmHg) with stirring. The drying process was stopped when the temperature reached the specified product temperature.

The product was removed from the mixer through the mill and was sieved and packed in fibre drums having a PE/alu foil lining and sealed by welding.

Procedure for Determining the Release Rate of Nicotine

The release of nicotine from nicotine delivery products were carried out according to the procedure set forth in the U.S.P. Official Monograph, Volume 25, pages 1225 and 1226.

Example A

State of the Art

Using the procedure stated above a mixture of nicotine and cation exchange resin and polyol of the state of the art (high water content) was produced from the constituents stated in the below table 1.

TABLE 1

| Constituent | Amount |
|---|---|
| Water 1 | 40.0 kg |
| Nicotine | 4.8 kg |
| Water 2 | 4.0 kg |
| Resin | 19.2 kg |
| Glycerol | 8.0 kg |
| Water 3 | 4.0 kg |
| Total Amount Added | 80.0 kg |
| Theoretical Dry Weight | 32.0 kg |
| Water Content at Start of Vacuum | 48.0 kg |

The water content was about 60% and the drying time until reaching the maximum temperature was about 10 hours.

Example 1

Using the procedure stated above a mixture of nicotine and cation exchange resin and polyol according to the invention was produced from the constituents stated in the below table 2.

TABLE 2

| Constituent | Amount |
|---|---|
| Water 1 | 10.8 kg |
| Nicotine | 4.8 kg |
| Water 2 | 4.0 kg |
| Resin | 19.2 kg |
| Glycerol | 8.0 kg |
| Water 3 | 2.4 kg |
| Total amount added | 49.2 kg |
| Theoretical Dry Weight | 32.0 kg |
| Water Content at Start of Vacuum | 17.2 kg |

The water content was about 35%, and the drying time until reaching the maximum temperature was about 3½ hours.

Example 3

Using the procedure stated above the release of nicotine from a product according to the invention was compared with the release from a product according to the state of the art. The results are stated in the below table 3.

TABLE 3

| Product | Release in percent |
|---|---|
| Example 1 | 82 |
| Example A | 79 |

As appears, the release of nicotine from the product of the invention is about the same as from the product made from a mixture having a high content of water.

The invention claimed is:

1. A method for preparing a nicotine delivery product; said method comprising:
   (a) mixing an aqueous suspension of a nicotine/cation exchange resin complex with glycerol or an aqueous solution or suspension thereof forming a mixture comprising a paste, wherein the total amount of water is from 26 to 45% by weight of the total mixture; wherein the resin is polacrilex; and
   (b) removing water from the paste to produce said nicotine delivery product having a release rate of 80% or more over a 10 minute time period.

2. The method as claimed in claim 1 wherein the total amount of water present in the paste is from 30 to 40% by weight of the total mixture.

3. The method as claimed in claim 2 wherein the total amount of water present in the paste is about 35% by weight of the total mixture.

4. A method for preparing a nicotine delivery product; said method comprising
   (a) mixing an aqueous solution of nicotine with a cation exchange resin forming a nicotine/cation exchange resin complex;
   (b) admixing to said complex of step (a) an aqueous solution or suspension of glycerol to form a mixture comprising a paste, wherein the nicotine/cation exchange resin complex incorporates the glycerol and the total amount of water is from 26 to 45% by weight of the total mixture; wherein the resin is polacrilex; and
   (c) removing water from said paste to produce said nicotine delivery product having a release rate of 80% or more over a 10 minute time period.

5. The method according to claim 4, wherein the concentration of nicotine in said aqueous solution of nicotine is from about 5% by weight to about 50% by weight.

6. The method according to claim 1, wherein the ratio of cation exchange resin to nicotine is from 1:1 to 10:1.

7. The method according to claim 6, wherein the ratio of cation exchange resin to nicotine is from 2:1 to 6:1.

8. The method according to claim 6, wherein the ratio of cation exchange resin to nicotine is about 4:1.

9. The method according to claim 1, wherein the ratio of cation exchange resin to glycerol is from 1:1 to 10:1.

10. The method according to claim 9, wherein the ratio of cation exchange resin to glycerol is from 2:1 to 8:1.

11. The method according to claim 9, wherein the ratio of cation exchange resin to glycerol is about 2.4:1.

12. A method for preparing a nicotine delivery product, said method comprising:
   (a) mixing an aqueous solution of nicotine with a cation exchange resin, wherein the resin is polacrilex;
      wherein the total amount of water is from 26 to 45% by weight of the total mixture;
   (b) admixing with said complex of step (a) glycerol to form a mixture comprising a paste wherein the nicotine/cation exchange resin complex incorporates the glycerol; and
   (c) removing water from said paste to produce said nicotine delivery product having a nicotine release rate of at least 80% over a 10 minute period.

13. The method of claim 1, wherein the nicotine delivery product has a release rate that is higher than a nicotine delivery product made by first mixing glycerol with ion exchange resin and then admixing nicotine to the glycerol-ion exchange resin mixture.

14. A method for preparing a nicotine delivery product; said method comprising:
   (a) mixing an aqueous suspension of a nicotine/cation exchange resin complex with an organic polyol or an aqueous solution or suspension thereof forming a mixture comprising a paste, wherein the total amount of water is from 26 to 45% by weight of the total mixture; wherein the resin is polacrilex; and (b) removing water from the paste to produce said nicotine delivery product having a release rate of 80% or more over a 10 minute time period.

* * * * *